US00PP32975P2

(12) United States Plant Patent
Hansen

(10) Patent No.: US PP32,975 P2
(45) Date of Patent: Apr. 13, 2021

(54) ***DIGITALIS* HYBRID PLANT NAMED 'FIRECRACKER'**

(50) Latin Name: ***Digitalis* x *Isoplexis***
Varietal Denomination: Firecracker

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,811

(22) Filed: Jul. 14, 2020

(51) Int. Cl.
*A01H 5/02* (2018.01)
*A01H 6/68* (2018.01)

(52) U.S. Cl.
USPC ..... Plt./263.1

(58) Field of Classification Search
USPC ..... Plt./263.1
See application file for complete search history.

(56) References Cited

PUBLICATIONS

Beechmount Garden Centre website (https://beechmount.ie/product/digiplexus-firecracker/). retrived Oct. 12, 2020. 6 pages (Year: 2020).*
Tuinadvies.be website (https://www.tuinadvies.be/plantengids/21093/digitalis-x-valinii-firecracker). retrived Oct. 20, 2020. 3 pages (Year: 2020).*

* cited by examiner

*Primary Examiner* — Susan McCormick Ewoldt
*Assistant Examiner* — Karen M Redden

(57) ABSTRACT

The new and distinct cultivar of intergeneric *Digitalis* hybrid plant named 'Firecracker' is characterized by sturdy, upright and dense habit with dark-green, serrate foliage and densely-branched flower stems with flowers that are open-faced, campanulate, self-cleaning, vivid yellowish-orange with reddish-purple undertones over a long period. The flowers produce an abundance of nectar and are attractive to hummingbirds in the landscape. The new plant is useful in the garden landscape, as a container plant or as a cut flower.

2 Drawing Sheets

Botanical designation: *Digitalis* x *Isoplexis*.
Cultivar denomination: 'Firecracker'.

STATEMENT REGARDING PRIOR DISCLOSURES UNDER 37 CFR 1.77(B)(6)

The first disclosure of the claimed plant, in the form of catalog advertisement by Gootjes-Allplant BV of The Netherlands on Aug. 20, 2019 followed by a posting on Mar. 3, 2020 by Walters Gardens, Inc. on their website. Information for these plants and subsequent plants for these sales were obtained from the inventor. No plants of *Digitalis* 'Firecracker' have been sold, in this country or anywhere in the world nor has any disclosure of the new plant been made more than one year prior the filing date of this application, and such sale or disclosure within one year was obtained either derived directly or indirectly from the inventor.

BACKGROUND OF THE INVENTION

The present invention relates to a new and distinct cultivar of hybrid plant, botanically known as *Digitalis ambigua* x *Isoplexis chalcantha*. The new *Digitalis* x *Isoplexis* 'Firecracker' is the product of a planned natural line breeding program conducted by the inventor at a wholesale perennial nursery in Zeeland, Mich., USA. The objective of the breeding program was to create novel intergeneric hybrid cultivars between *Digitalis ambigua* and *Isoplexis chalcantha* with excellent flowers, foliage and habit.

The new intergeneric *Digitalis* hybrid was a planned cross between a proprietary selection of the seed cultivar *Digitalis*

*ambigua* 'Carillon' (not patented) as the female or seed parent times a proprietary selection of *Isoplexis chalcantha* (not patented) as the male or pollen parent on Feb. 9, 2012 and later assigned the breeder code of 12-18-19. After further evaluation 'Firecracker' was selected as a single plant from among several hundred crosses between various forms of such *Digitalis* x *Isoplexis* hybrids and first asexually propagated by basal shoot cuttings in the summer of 2013 at the same wholesale perennial nursery in Zeeland, Mich. The new plant has since also been successfully asexually propagated by sterile shoot tip tissue culture. All of the resultant asexually propagated plants by cuttings and tissue culture have remained stable and reproduced true to type in successive generations.

SUMMARY OF THE INVENTION

Plants of the foxglove plant cultivar *Digitalis* x *Isoplexis* 'Firecracker' have not been observed under all possible environmental conditions. The phenotype may vary somewhat with variations in. environment such as fertilizer, temperature, light intensity and photoperiod and plant growth regulators without, however, any variance in genotype.

The following traits in combination with one another have been repeatedly observed and are determined to be the unique characteristics of 'Firecracker':

1. Sturdy, upright and dense growth habit.
2. High number of stiff basal branches extending bloom season from early summer till frost.

3. Medium, open-faced, campanulate-formed, horizontal-facing, long-blooming, self-cleaning, non-secund flowers of vivid yellowish-orange with reddish-purple undertones;
4. Narrow, gray-green, sparsely-pubescent, mostly-basal, serrate leaves.

Plants of the new *Digitalis* can be compared to the female parent, *Digitalis ambigua* 'Carillon' has longer and broader flowers of creamy-yellow on shorter plants and the flowering season is much shorter. The male parent has dark, glossy, glabrous foliage with shrub-like habit with less branching of the flower stems, and the flowers are deeper reddish-orange in color on darker stems. The new plant is also more herbaceous producing more basal rosettes and branches than the male parent which is less branched and more shrub-like. Other closely comparable plants include, 'Berry Canary' U.S. Plant Pat. No. 27,607, 'Firebird' U.S. Plant Pat. No. 31,840, 'Flame' (not patented), 'DG 09/4' U.S. Plant Pat. No. 25,442, 'Dusty Maid' (not patented) and 'Sunset' (not patented). *Digitalis* 'Berry Canary' U.S. Plant Pat. No. 17,849 has a slightly taller habit and larger flowers of purplish rose with light yellow throats with burgundy speckling into a taller plant. 'Firebird' has a taller and broader habit, and flowers of coppery-pink with soft orange throats having pinkish purple spotting. 'Flame' has a taller and broader habit with flowers of more pinkish-lavender and soft yellowish-orange throat with pinkish-lavender spotting. 'DG 09/04' has petals with an outer surface color of dark pink with apricot undertones and the inner surface of yellowish orange with dark pink margins and dark pink spotting. 'Dusty Maid' has flowers that are burgundy on the outside with yellow center and reddish-burgundy margins and veins, and the petal apices are rounded. 'Sunset' has flowers of rusty pinkish-purple with centers of orangish-amber and reddish veined and spotted. All of the above comparison varieties have larger flowers than Firecracker.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plants used in the drawings are second-year growing plants following a vernalization period of about 8 weeks, grown in a greenhouse at a wholesale nursery in Zeeland, Mich. with supplemental fertilizer but without plant growth regulators.

DETAILED BOTANICAL DESCRIPTION

Figure 1:
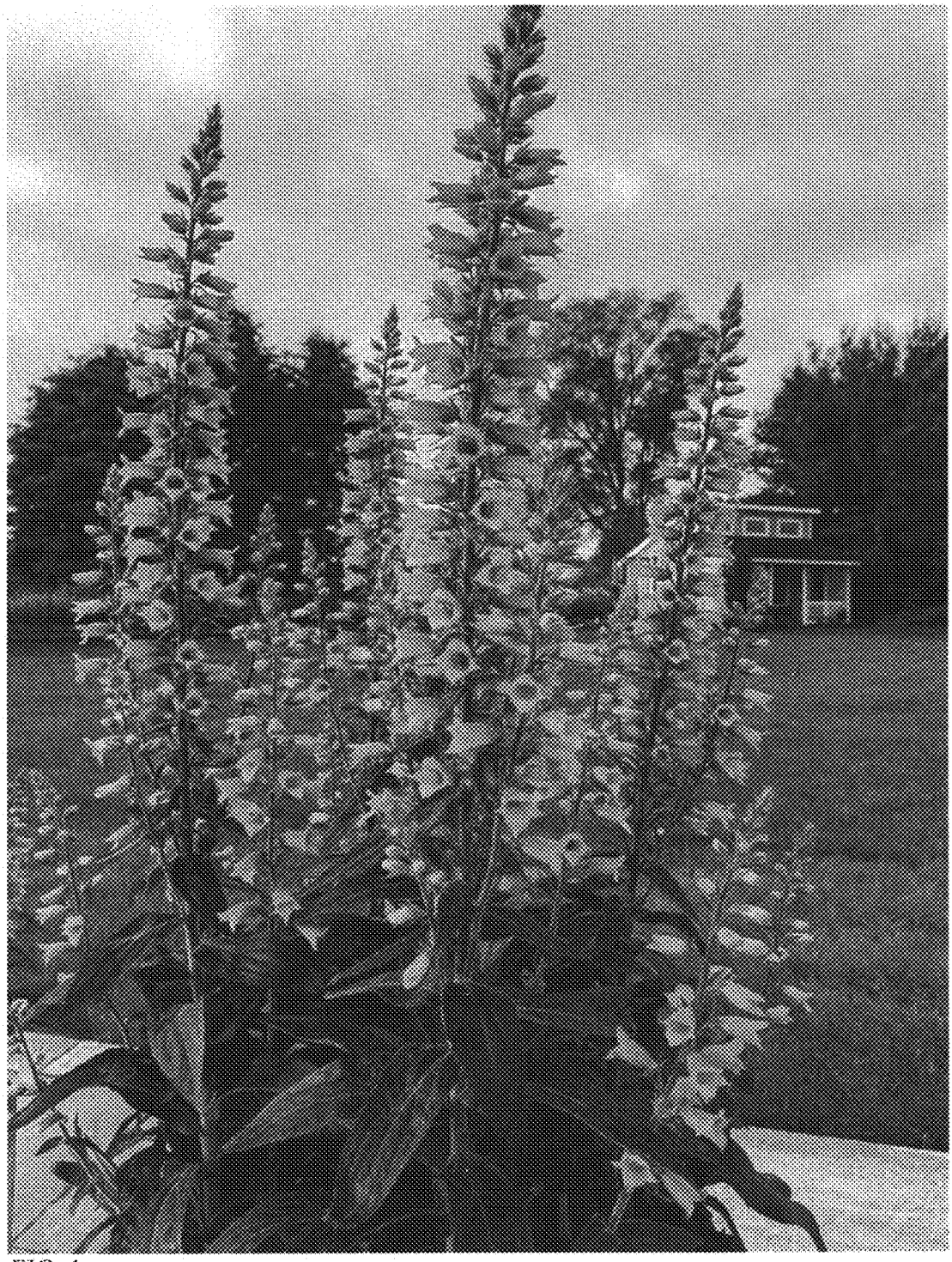
FIG. 1 shows the plant compact, dense, upright, flowering habit of a two-year-old plant.
Figure 2:
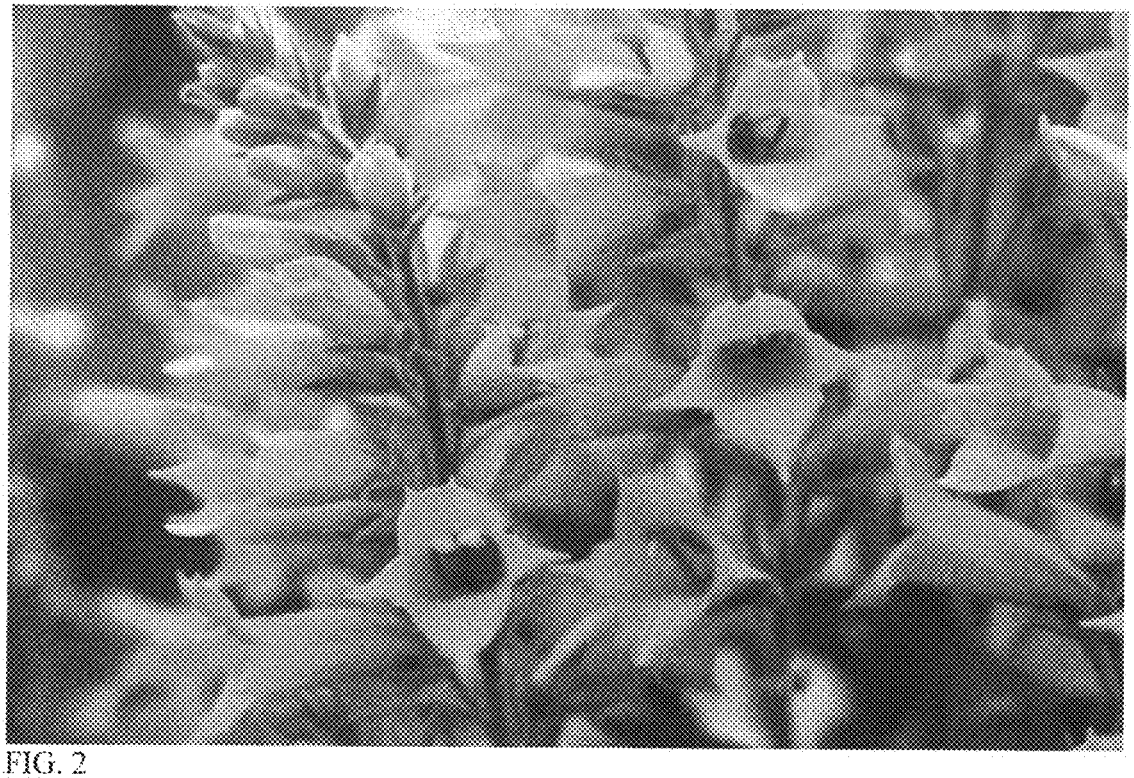
FIG. 2 shows a close-up of the flowers on the scape.

The following descriptions and color references are based on the 2015 edition of The Royal Horticultural Society Colour Chart except where common dictionary terms are used. The new plant, *Digitalis* x *Isoplexis* 'Firecracker', has not been observed under all possible environments. The phenotype may vary slightly with different environmental conditions, such as temperature, light, fertility, moisture and maturity levels, but without any change in the genotype. The following observations and size descriptions are of two-year-old plants in both the greenhouses and loamy-sand open field trials of a nursery in Zeeland, Mich. with supplemental fertilizer and water as needed. The outdoor plants are not treated with plant growth regulators, nor were they pinched at any time in the growth year. The greenhouse-grown plants were treated once with a growth retardant. Flower bud and flower color differ in the two growing conditions while other traits remain identical.

Parentage: Female, or seed parent an unnamed and unreleased selection of *Digitalis ambigua* 'Carillion'; male, or pollen parent an unnamed, unreleased selection of *Isoplexis chalcantha;*

Propagation: Method: shoot tip cuttings and sterile shoot tip plant tissue culture division.

Root description: Fine, freely branching; color creamy white near RHS 15D;

Time to initiate roots from tissue culture: About two weeks;

Crop time: Under normal cool spring growing conditions of 12° to 15° C., finished flowering plants can be obtained in about 8 to 10 weeks from a vernalized 25 mm plug;

Plant vigor: Very good;

Plant habit: Perennial, hardy from at least USDA zone 8 through 10 but capable of growing in colder regions as an annual; upright and dense; leaves cauline and alternate; tightly arranged, nodes about 5.0 mm apart in lower stem and 2.2 cm in upper portion before flowers, average about 8.0 mm apart; size with flowers about 88.0 cm tall and 42.0 cm across at widest point with branches;

Main stem: Stiff and erect; about 88.0 cm long and 2.0 cm diameter at base; densely puberulent; cylindrical with basal portion having ridges extended from central leaf veins; length of ridges extends to next lower leaf directly below; with basal branches and axillary branches;

Main stem color: Lower portion nearest RHS 145C and the upper portion in higher light exposure between RHS N186C and RHS 79B;

Primary branches: Upright next to main stem; to about 55 cm long and 7.0 mm diameter; lightly puberulent; about eight per plant; color and tinting same as main stem;

Axillary (secondary) branches: About two per plant; nearly erect; about 17 cm long and 3.0 mm diameter at base; puberulent; flowering from secondary branches arising from nodes just below lowest flowers and successively continuing lower at each node; same color as main branch;

Foliage: Cauline and dextrorse to alternate; sessile; to about 20.0 cm long at base and 5.3 cm wide at widest point, average about 15.0 cm long and 3.5 cm; about 120 leaves per plant below initial flowers;

Leaf blade: Cuneate, with acute apex and attenuate to sessile base; very lightly puberulent on both surfaces; serrate to serrulate in distal region; lustrous above and slightly lustrous below;

Leaf blade color: Adaxial nearest RHS 139A, abaxial nearest RHS 137C;

Veins: Pinnate; puberulent abaxial and sparsely puberulent adaxial; ridged on bottom and slightly impressed above;

Vein color: Adaxial nearest RHS 139A; abaxial midrib and primary veins nearest RHS 146D, secondary veins and perimeter veins nearest RHS NN137C;

Flower: Campanulate, total corolla average size 3.0 cm long and face opening to 2.4 cm across and 2.0 cm tall, with basal 2.0 cm of corolla tube fused and to about 12.0 mm wide and 11.0 mm tall at fusion; zygomorphic; with four main lobes, two side lobes smallest and nearly perpendicular to upper and lower lobes, lowest lobe longest and upper lobe widest; two side lobes about 5.0 mm wide at fusion and 26.0 mm long with broadly acute apex; upper lobe about 10.0 mm wide at fusion and 26.0 mm long with emarginate apex with lobes acute; lowest lobe about 13.0 mm wide at fusion and 26.0 mm long, apex typically acute; length of side lobes from fusion to apex about 6.0 mm, top lobe length from fusion to apex about 8.0 mm and lowest lobe length from fusion to apex about 10.0 mm; side and lower lobes rarely with single 1.0 mm long tooth at base before corolla fusion; speckling or flecking absent on adaxial of the petal surfaces; lowest lobe and side lobes puberulent on abaxial surfaces and distal portion of adaxial surfaces; upper lobe glabrous on adaxial and abaxial surfaces; not persistent, self-cleaning; produces large amount of nectar;

Flower number: About 50 per main stem, about 45 per lateral branch and about 33 per axillary branch;

Flower bud: Oblong tubular; to about 19.0 mm long and 7.0 mm diameter near middle and about 4.5 mm diameter near base; apex and base rounded;

Flower bud color in greenhouse: Nearest a blend between RHS 31C and RHS N170C distally with slight blush of RHS 82A, proximally nearest RHS 150D;

Flower bud color in full sun: Nearest RHS 23D, ventrally with undertones of nearest RHS 145B proximally;

Flower color in greenhouse: Varies with maturity; shortly after opening—ventral abaxial between RHS 179D and RHS 164D, dorsal abaxial nearest RHS 181C, and adaxial distally nearest RHS 164C and adaxial proximally nearest RHS 164D; at pollen dehiscence about five days after opening abaxial dorsal nearest RHS N34A, abaxial ventral between RHS N34A and RHS 34B, adaxial lower lobe nearest RHS N163C with veins and distal blushing of nearest RHS 173A, side and upper lobes nearest RHS 178A and RHS 170A; prior to dehiscence abaxial dorsal nearest RHS 178C and RHS 181B and ventral nearest RHS 167D, adaxial lower and side lobes nearest a blend between RHS N163D and RHS 167B, upper lobe nearest RHS 167B with proximal blushing of nearest RHS173B;

Flower color in full sun: Varies slightly with maturity; shortly after opening—ventral abaxial between RHS 23D and RHS 23C, dorsal abaxial between RHS 26C and RHS 26B, and adaxial nearest RHS 23B with veins nearest RHS 31B; at pollen dehiscence about four to five days after opening ventral abaxial between RHS 26B and RHS 26C, dorsal abaxial between RHS 34C and RHS 34D, adaxial nearest RHS 26B with veins of nearest RHS 31B; prior to flower drop abaxial ventral nearest RHS 26C and abaxial dorsal between RHS 26C and RHS 26D, adaxial nearest RHS 26C with veins of nearest RHS 26D;

Inflorescence: Average size 52.0 cm long and 22.0 cm wide with side branches;

Flower bract: Deltoid to lanceolate; sharply acute apex and truncate sessile base; margin finely serrate; adaxial and abaxial finely puberulent; to about 2.4 cm long and 1.0 cm across near middle, decreasing distally;

Flower bract color: Adaxial nearest RHS NN137A, abaxial nearest RHS 137A;

Natural flowering season: Early summer through frost;

Flower longevity: Individual flowers on plant lasting about 7 to 10 days; main flower spike stays in flower for at least three months under ideal conditions;

Fragrance: None detected;

Sepals: Five; persistent; lanceolate; acute apex, truncate base, entire and puberulent margin; puberulent abaxial and adaxial; about 12.0 mm long and 4.0 cm across at middle;

Sepal color: Adaxial and abaxial surfaces nearest a blend between RHS 146C and RHS 138A;

Peduncle: Strong, erect; puberulent; about 88.0 cm long and 8.0 mm in diameter below first flowers; color lower portion nearest RHS 145C and the upper portion in higher light exposure between RHS N186C and RHS 79B;

Pedicel: Puberulent; cylindrical; erect to 45 degree angle at flower anthesis; to 13.0 mm long and 1.7 mm diameter; color nearest RHS 137B with low light exposure and nearest RHS N186C in high light exposure;

Gynoecium: Single; about 25.0 mm long;

*Style*.—Arcuate downward; lustrous; about 19.0 mm long and gradually tapering from ovary to stigma to about 0.7 mm diameter, color nearest RHS 160D toward stigma and nearest RHS N186C toward ovary.

*Stigma*.—Acute; to about 1.0 mm long and about 0.5 mm wide; color lighter than RHS 4B.

*Ovary*.—Superior; puberulent; long, conical, apex tapering to meet style; about 6.0 mm long and 3.0 mm across at base; color nearest RHS 144B.

Androecium: Four, didynamous; further extending set dehiscing first;

*Filaments*.—Four; flattened and arcuate along inside of petal; basal 3.0 mm adnate to petal; about 15.0 mm and 19.0 mm long and 1.0 mm diameter at base; color nearest RHS N186D.

*Anther*.—Further extending set dehiscing first; divergent dorsifixed; each half about 2.5 mm long and each half about 1.0 mm across; color prior to dehiscence between RHS 4B.

*Pollen*.—Abundant, dust-like; color nearest RHS 158C.

Fruit: Mature seed pods rarely produced; and viable seed production have not yet been observed;

Seed: Viable seed production has not yet been observed;

Disease and pest resistance or tolerance: 'Firecracker' is not normally bothered by rodents or deer in the landscape. Disease or pest resistance beyond that typical of other *Digitalis* hybrids has not been noted. The new plant performs best in full sun to slight shade with good drainage and regular watering.

Hardiness: The new plant is winter hardy to approximately USDA zone 8, but requires a vernalization period for best flower production.

It is claimed:

1. A new and distinct cultivar of *Digitalis* hybrid plant named 'Firecracker' as illustrated and described.

* * * * *